(12) United States Patent
Campochiaro

(10) Patent No.: US 7,268,137 B2
(45) Date of Patent: *Sep. 11, 2007

(54) OCULAR THERAPY

(76) Inventor: Peter A. Campochiaro, 920 W. Lake Ave., Baltimore, MD (US) 21210

( * ) Notice: Subject to any disclaimer, the term of this patent is extended or adjusted under 35 U.S.C. 154(b) by 0 days.

This patent is subject to a terminal disclaimer.

(21) Appl. No.: 10/704,297

(22) Filed: Nov. 7, 2003

(65) Prior Publication Data

US 2004/0116434 A1 Jun. 17, 2004

Related U.S. Application Data

(60) Provisional application No. 60/424,609, filed on Nov. 7, 2002.

(51) Int. Cl.
*A61K 31/50* (2006.01)
(52) U.S. Cl. ........................ 514/249; 514/912
(58) Field of Classification Search ............... 514/249, 514/912
See application file for complete search history.

(56) References Cited

U.S. PATENT DOCUMENTS

| | | |
|---|---|---|
| 6,258,812 B1 | 7/2001 | Bold et al. |
| 6,514,974 B2 | 2/2003 | Bold et al. |
| 6,710,047 B2 | 3/2004 | Bold et al. |
| 2003/0171375 A1 | 9/2003 | Brazzell |

FOREIGN PATENT DOCUMENTS

| | | | |
|---|---|---|---|
| WO | WO97/34876 | * | 9/1997 |
| WO | WO97/34920 | * | 9/1997 |
| WO | WO98/35958 | | 8/1998 |

* cited by examiner

*Primary Examiner*—Zohreh Fay
(74) *Attorney, Agent, or Firm*—Novartis; John B. Alexander

(57) ABSTRACT

A method for treating a subject suffering from epiretinal membrane formation or retinal detachment due to epiretinal membrane formation is disclosed. The method comprises administering a compound of the formula:

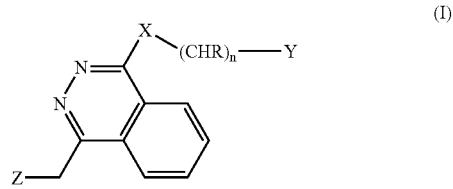

(I)

wherein
n is 0 to 2,
R is H or lower alkyl;
X is imino, oxa, or thia;
Y is aryl; and
Z is unsubstituted or substituted pyridyl,
an N-oxide thereof, wherein 1 or more N atoms carry an oxygen atom,
or a salt thereof.

13 Claims, No Drawings

OCULAR THERAPY

Epiretinal membrane (ERM) formation is a proliferation of cells in the retina that causes the production of sheets of cells and extracellular matrix that exert traction on the retina. ERM formation is a common cause of visual impairment. Mild ERMs cause wrinkling and distortion of the retina, and when the macula is involved, this results in metamorphopsia and mild to moderate decreased vision. Severe ERMs result in retinal detachment and severe visual loss, and unless corrected by vitreous surgery can cause blindness.

Increased expression of vascular endothelial growth factor (VEGF) is both necessary and sufficient for the development of retinal neovascularization. The new blood vessels lay down extracellular matrix and recruit glial cells and retinal pigmented epithelial (RPE) cells, resulting in ERMs that can obscure the retina and/or detach it. PDGF is a potent chemoattractant for retinal glia and RPE cells. PDGF B-chain (PDGF-B) is produced by endothelial cells, and endothelial-cell derived PDGF-B is necessary for pericyte recruitment during vascular development. Transgenic mice in which the rhodopsin promoter drives expression of PDGF-B in photoreceptors (rho/PDGF-B mice) develop epiretinal membranes consisting of glial cells, endothelial cells, and pericytes that cause traction retinal detachment within 2-3 weeks of the onset of transgene expression. The cellular components are similar to those in diabetic membranes and therefore, rho/PDGF-B mice provide a useful model of diabetic traction retinal detachment.

PDGF A-chain (PDGF-A) is produced by retinal ganglion cells and vascular cells and during development PDGF-A stimulates migration of astrocytes into the retina from the optic nerve. The expression of PDGFs in the retina is reduced in adults, but retinal detachment results in increased production of PDGFs by RPE cells, and several lines of evidence have implicated PDGF-A in proliferative vitreoretinopathy (PVR), a disease process in which ERMs and traction retinal detachment occur after retinal reattachment surgery. Transgenic mice in which the rhodopsin promoter drives expression of PDGF-A in photoreceptors (rho/PDGF-A mice) develop epiretinal membranes consisting solely of glial cells. Homozygous rho/PDGF-A mice develop slowly progressive retinal detachment, and after detachment there is proliferation of RPE cells resulting in subretinal membranes, and eventually a funnel-shaped detachment. This model mimics many aspects of PVR.

DETAILED DESCRIPTION OF THE INVENTION

It has now been unexpectedly discovered that receptor kinase inhibitors can treat traction retinal detachment due to ERM formation.

The invention is directed to methods for the treatment of a subject suffering from ERM formation or retinal detachment due to ERM formation comprising administering to a subject suffering from ERM formation or retinal detachment due to ERM formation an effective amount of a compound of formula I to treat ERM formation or retinal detachment in the eye of the subject, wherein formula I is

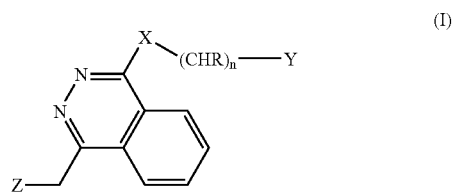

wherein
n is 0 to 2,
R is H or lower alkyl;
X is imino, oxa, or thia;
Y is aryl; and
Z is unsubstituted or substituted pyridyl,
an N-oxide thereof, wherein 1 or more N atoms carry an oxygen atom,
or a salt thereof.

The invention also includes methods for the treatment of a subject suffering from ERM formation or retinal detachment due to ERM formation comprising administering to a subject suffering from ERM formation or retinal detachment due to ERM formation an effective amount of a compound of formula I in combination with another compound or agent that inhibits the activity of VEGF to treat ERM formation or retinal detachment in the eye of the subject. Such other compounds and agents are known to those of skill in the art, and include, e.g., the compound N-benzoyl staurosporine (referred to herein as PKC412) and other compounds disclosed in U.S. Pat. No. 6,214,819, hereby incorporated herein in its entirety.

As indicated above and below the addressed compounds are in particular useful in the treatment of ERM formation and subsequent retinal detachment.

The general terms used hereinbefore and hereinafter preferably have within the context of this disclosure the following meanings, unless otherwise indicated:

To "treat ERM formation" as used herein means to decrease the amount of ERM formation in the eye of a subject suffering from or likely to suffer from ERM formation. To "treat retinal detachment" means to reduce the degree to which the retina detaches in a subject suffering from ERM, up to and including prevention of detachment.

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms (for example in compounds of formula I (or an N-oxide thereof), wherein n=1 and R is lower alkyl) may be present in the (R)-, (S)- or (R,S)-configuration, preferably in the (R)- or (S)-configuration. Substituents at a double bond or a ring may be present in cis-(=Z-) or trans (=E-) form. The compounds may thus be present as mixtures of isomers or as pure isomers, preferably as enantiomer-pure diastereomers.

The index n is preferably 0 or 1, especially 0.

Lower alkyl is especially C1-C4-alkyl, e.g. n-butyl, sec-butyl, tert-butyl, n-propyl, isopropyl, or especially methyl or also ethyl.

In the preferred embodiment, aryl is an aromatic moiety having 6 to 14 carbon atoms, especially phenyl, naphthyl, fluorenyl or phenanthrenyl, the moieties defined above being unsubstituted or substituted by one or more, preferably up to three, especially one or two substituents, especially selected from amino, mono- or disubstituted amino, halogen, alkyl, substituted alkyl, hydroxy, etherified or esterified hydroxy, nitro, cyano, carboxy, esterified carboxy, alkanoyl, carbamoyl, N-mono- or N,N-disubstituted carbamoyl, amidino, guanidino, mercapto, sulfo, phenylthio, phenyl-lower alkylthio, alkylphenylthio, phenylsulfinyl, phenyl-lower alkylsulfinyl, alkylphenylsulfinyl, phenylsulfonyl, phenyl-lower alkylsulfonyl, and alkylphenylsulfonyl, or (as an alternative or in addition to the above group of substituents) selected from lower alkenyl, such as ethenyl, phenyl, lower alkylthio, such as methylthio, lower alkanoyl, such as acetyl, lower alkylmercapto, such as methylmercapto (—S—CH3), halogen-lower alkylmercapto, such as trifluoromethylmercapto (—S—CF3), lower alkylsulfonyl, halogen-lower alkylsulfonyl, such as especially trifluoromethane sulfonyl, dihydroxybora (—B(OH)2), heterocyclyl, and lower alkylene dioxy bound at adjacent C-atoms of the ring, such as methylene dioxy; aryl is preferably phenyl which is either unsubstituted or independently substituted by one or two substituents selected from the group comprising amino; lower alkanoylamino, especially acetylamino; halogen, especially fluorine, chlorine, or bromine; lower alkyl, especially methyl or also ethyl or propyl; halogen-lower alkyl, especially trifluoromethyl; hydroxy; lower alkoxy, especially methoxy or also ethoxy; phenyl-lower alkoxy, especially benzyloxy; and cyano, or (as an alternative or in addition to the previous group of substituents) C8-C12alkoxy, especially n-decyloxy, carbamoyl, lower alkylcarbamoyl, such as n-methyl- or n-tert-butylcarbamoyl, lower alkanoyl, such as acetyl, phenyloxy, halogen-lower alkyloxy, such as trifluoromethoxy or 1,1,2,2-tetrafluoroethyloxy, lower alkoxycarbonyl, such as ethoxycarbonyl, lower alkylmercapto, such as methylmercapto, halogen-lower alkylmercapto, such as trifluoromethylmercapto, hydroxy-lower alkyl, such as hydroxymethyl or 1-hydroxymethyl, lower alkylsulfonyl, such as methane sulfonyl, halogen-lower alkylsulfonyl, such as trifluoromethane sulfonyl, phenylsulfonyl, dihydroxybora (—B(OH)2), 2-methylpyrimidin-4-yl, oxazol-5-yl, 2-methyl-1,3-dioxolan-2-yl, 1H-pyrazol-3-yl, 1-methyl-pyrazol-3-yl and lower alkylene dioxy bound to two adjacent C-atoms, such as methylene dioxy.

Where mention is made hereinbefore and hereinafter to moieties or substituents as "an alternative or in addition to" the previous group of moieties or substituents, these moieties or substituents and those of the previous group are to be regarded together as one group of substituents from which the respective moieties may be selected, or especially as separate groups. The expression does not mean that one of the radicals following the expression may be added to a member of the previous group by binding. This applies, even if the expression "as an alternative or in addition to" is not mentioned again, for the moieties or substituents, as defined here, in the preferred compounds of formula I defined below.

Mono- or disubstituted amino is especially amino substituted by one or two moieties selected independently of one another from lower alkyl, such as methyl; hydroxy-lower alkyl, such as 2-hydroxyethyl; phenyl-lower alkyl; lower alkanoyl, such as acetyl; benzoyl; substituted benzoyl, wherein the phenyl moiety is unsubstituted or especially substituted by one or more, preferably one or two, substituents selected from nitro or amino, or also from halogen, amino, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl moiety is unsubstituted or especially substituted by one or more, preferably one or two, substituents selected from nitro or amino, or also from halogen, amino, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl moiety in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl or carbamoyl, or as an alternative or in addition to the previous group of moieties by aminocarbonylamino.

Halogen is preferably fluorine, chlorine, bromine, or iodine, more preferably fluorine, chlorine, or bromine.

In the preferred embodiment, alkyl has up to a maximum of 12 carbon atoms and is preferably lower alkyl, more preferably methyl, ethyl, n-propyl, isopropyl, or tert-butyl.

Substituted alkyl is alkyl as last defined, especially lower alkyl, preferably methyl; where one or more, especially up to three, substituents may be present, primarily from the group selected from halogen, especially fluorine, and also from amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred.

Etherified hydroxy is especially C8-C20alkyloxy, such as n-decyloxy, lower alkoxy, such as methoxy, ethoxy, isopropyloxy, or n-pentyloxy, phenyl-lower alkoxy, such as benzyloxy or phenyloxy, or as an alternative or in addition to the previous group C8-C20alkyloxy, such as n-decyloxy, halogen-lower alkoxy, such as trifluoromethyloxy or 1,1,2,2-tetrafluoroethoxy.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-mono- or N,N-disubstituted carbamoyl is especially substituted by one or two substituents, lower alkyl, phenyl-lower alkyl, or hydroxy-lower alkyl, at the terminal nitrogen atom.

Alkylphenylthio is especially lower alkylphenylthio.

Alkylphenylsulfinyl is especially lower alkylphenylsulfinyl.

Alkylphenylsulfinyl is especially lower alkylphenylsulfinyl.

Unsubstituted pyridyl is preferably 3- or 4-pyridyl. Specially preferred is 4-pyridyl.

Substituted pyridyl is preferably 3- or 4-pyridyl which is substituted by one or two substituents, in particular selected from lower alkyl, preferably methyl, ethyl; halogen preferably chloro, fluoro, bromo; lower alkyl halides preferably trifluoromethyl; lower alkoxy preferably methoxy, ethoxy; hydroxy; cyano; amino, N-lower alkylamino, N,N-di-lower alkylamino. Specially preferred is 4-pyridyl substituted by methyl, chloro, fluoro, trifluoromethyl or methoxy.

Heterocyclyl is especially a five or six-membered heterocyclic system with 1 or 2 heteroatoms selected from the group comprising nitrogen, oxygen, and sulfur, which may be unsaturated or wholly or partly saturated, and is unsubstituted or substituted especially by lower alkyl, such as methyl; a moiety selected from 2-methylpyrimidin -4-yl, oxazol-5-yl, 2-methyl-1,3-dioxolan-2-yl, 1H-pyrazol-3-yl, and 1-methyl-pyrazol-3-yl is preferred.

Aryl in the form of phenyl which is substituted by lower alkylene dioxy bound to two adjacent C-atoms, such as methylenedioxy, is preferably 3,4-methylenedioxyphenyl.

An N-oxide of a compound of formula I is preferably an N-oxide in which a phthalazine-ring nitrogen or a nitrogen in the pyridin ring carries an oxygen atom, or several of the said nitrogen atoms carry an oxygen atom.

Salts are especially the pharmaceutically acceptable salts of compounds of formula I (or an N-oxide thereof).

When a basic group and an acid group are present in the same molecule, a compound of formula I (or an N-oxide thereof) may also form internal salts.

With the groups of preferred compounds of formula I mentioned hereinafter, definitions of substituents from the general definitions mentioned hereinbefore may reasonably be used, for example, to replace more general definitions with more specific definitions or especially with definitions characterized as being preferred.

Preference is given to a compound of formula I wherein n is 0 or 1,

R is H or lower alkyl, especially H or methyl,

X is imino, oxa, or thia,

Y is phenyl, which is unsubstituted or is substituted by one or two substituents independently of one another from the group comprising amino; lower alkanoylamino, especially acetylamino; halogen, especially fluorine, chlorine, or bromine; lower alkyl, especially methyl or also ethyl or propyl; halogen-lower alkyl, especially trifluoromethyl; hydroxy; lower alkoxy, especially methoxy or also ethoxy; phenyl-lower alkoxy, especially benzyloxy; and cyano, or (as an alternative or in addition to the previous group of substituents) lower alkenyl, such as ethenyl, C8-C12alkoxy, especially n-decyloxy, lower alkoxycarbonyl, such as tert-butoxycarbonyl, carbamoyl, lower alkylcarbamoyl, such as N-methyl- or N-tert-butylcarbamoyl, lower alkanoyl, such as acetyl, phenyloxy, halogen-lower alkyloxy, such as trifluoromethoxy or 1,1,2,2-tetrafluoroethyloxy, lower alkoxycarbonyl, such as ethoxycarbonyl, lower alkylmercapto, such as methylmercapto, halogen-lower alkylmercapto, such as trifluoromethylmercapto, hydroxy-lower alkyl, such as hydroxymethyl, lower alkylsulfonyl, such as methanesulfonyl, halogen-lower alkylsulfonyl, such as trifluoromethanesulfonyl, phenylsulfonyl, dihydroxybora (—B(OH)2), 2-methylpyrimidin-4-yl, oxazol-5-yl, 2-methyl-1,3-dioxolan-2-yl, 1h-pyrazol-3-yl, 1-methyl-pyrazol-3-yl and lower alkylenedioxy bound to two adjacent C-atoms, such as methylenedioxy, or is also pyridyl, especially 3-pyridyl; especially phenyl, 2-, 3- or 4-aminophenyl, 2-, 3- or 4-acetylaminophenyl, 2-, 3- or 4-fluorophenyl, 2-, 3- or 4-chlorophenyl, 2-, 3- or 4-bromophenyl, 2,3-, 2,4-, 2,5- or 3,4-dichlorophenyl, chlorofluorophenyl, such as 3-chloro-4-fluorophenyl or also 4-chloro-2-fluoroanilino, 2, -3- or 4-methylphenyl, 2-, 3- or 4-ethylphenyl, 2-, 3- or 4-propylphenyl, methylfluorophenyl, such as 3-fluoro-4-methylphenyl, 2-, 3- or 4-trifluoromethylphenyl, 2-, 3- or 4-hydroxyphenyl, 2-, 3- or 4-methoxyphenyl, 2-, 3- or 4-ethoxyphenyl, methoxychlorophenyl, such as 3-chloro-4-methoxycarbonyl, 2-, 3- or 4-benzyloxyphenyl, 2-, 3- or 4-cyanophenyl, or also 2-, 3- or 4-pyridyl; and Z is 3- or 4-pyridyl, which is unsubstituted or is substituted by one or two substituents independently of one another from the group comprising halogen, especially fluorine, chlorine, or bromine; lower alkyl, especially methyl or also ethyl or propyl; halogen-lower alkyl, especially trifluoromethyl; hydroxy; lower alkoxy, especially methoxy or also ethoxy.

Special preference is given to a compound of formula I, n is 0 or 1,

R is H,

X is imino,

Y is phenyl, which is unsubstituted or is substituted by one or two substituents independently of one another from the group comprising amino; lower alkanoylamino, especially acetylamino; halogen, especially fluorine, chlorine, or bromine; lower alkyl, especially methyl; halogen-lower alkyl, especially trifluoromethyl; hydroxy; lower alkoxy, especially methoxy; phenyl-lower alkoxy, especially benzyloxy; and cyano; especially phenyl, 2-, 3- or 4-aminophenyl, 2-, 3- or 4-acetylaminophenyl, 2-, 3- or 4-fluorophenyl, 2-, 3- or 4-chlorophenyl, 2-, 3- or 4-bromophenyl, 2,3-, 2,4-, 2,5- or 3,4-dichlorophenyl, chlorofluorophenyl, such as 3-chloro-4-fluorophenyl, 2, -3- or 4-methylphenyl, 2-, 3- or 4-trifluoromethylphenyl, 2-, 3- or 4-hydroxyphenyl, 2-, 3- or 4-methoxycarbonyl, methoxychlorophenyl, such as 3-chloro-4-methoxycarbonyl, 2-, 3- or 4-benzyloxyphenyl, or 2-, 3- or 4-cyanophenyl; and Z is 4-pyridyl, which is unsubstituted or is substituted by a substituent from the group consisting of halogen, especially fluorine, chlorine, or bromine; lower alkyl, especially methyl or also ethyl or propyl; halogen-lower alkyl, especially trifluoromethyl; hydroxy; lower alkoxy, especially methoxy.

Special preference is also given to a compound of formula I, n is 0 or 1,

R is H,

X is imino,

Y is phenyl, which is unsubstituted or is substituted by one or two substituents independently of one another from the group comprising halogen, especially fluorine, chlorine, or bromine; lower alkyl, especially methyl; halogen-lower alkyl, especially trifluoromethyl; hydroxy; lower alkoxy, especially methoxy; cyano; and Z is 4-pyridyl, which is unsubstituted or is substituted by a substituent from the group consisting of halogen, especially fluorine, or chlorine; lower alkyl, especially methyl; halogen-lower alkyl, especially trifluoromethyl; hydroxy; lower alkoxy, especially methoxy.

Special preference is also given to a compound of formula I, n is 0,

X is imino,

Y is phenyl, which is unsubstituted or is substituted by one substituent selected from the group consisting of fluorine, chlorine; methyl; trifluoromethyl; hydroxy; cyano and methoxy; and Z is 4-pyridyl, which is unsubstituted or is substituted by a substituent selected from the group consisting of fluorine, or chlorine; methyl; trifluoromethyl; hydroxy; methoxy.

Special preference is also given to a compound of formula I,
n is 0,
X is imino,
Y is phenyl, which is unsubstituted or is substituted by one substituent selected from the group consisting of fluorine, chlorine; methyl; methoxy; cyano and trifluoromethyl; and
Z is 4-pyridyl, which is unsubstituted or is substituted by a substituent selected from the group consisting of fluorine, or chlorine; and methyl.

High preference is given to a compound selected from the group consisting of:
1-(4-Chloroanilino)-4-(4-pyridylmethyl)phthalazine;
1-(3-Chloroanilino)-4-(4-pyridylmethyl)phthalazine;
1-Anilino-4-(4-pyridylmethyl)phthalazine;
1-Benzylamino-4-(4-pyridylmethyl)phthalazine;
1-(4-Methoxyanilino)-4-(4-pyridylmethyl)phthalazine;
1-(3-Benzyloxyanilino)-4-(4-pyridylmethyl)phthalazine;
1-(3-Methoxyanilino)-4-(4-pyridylmethyl)phthalazine;
1-(2-Methoxyanilino)-4-(4-pyridylmethyl)phthalazine;
1-(4-Trifluoromethylanilino)-4-(4-pyridylmethyl)phthalazine;
1-(4-Fluoroanilino)-4-(4-pyridylmethyl)phthalazine;
1-(3-Hydroxyanilino)-4-(4-pyridylmethyl)phthalazine;
1-(4-Hydroxyanilino)-4-(4-pyridylmethyl)phthalazine;
1-(3-Aminoanilino)-4-(4-pyridylmethyl)phthalazine;
1-(3,4-Dichloroanilino)-4-(4-pyridylmethyl)phthalazine;
1-(4-Bromoanilino)-4-(4-pyridylmethyl)phthalazine;
1-(3-Chloro-4-methoxyanilino)-4-(4-pyridylmethyl)phthalazine;
1-(4-Cyanoanilino)-4-(4-pyridylmethyl)phthalazine;
1-(4-Methylanilino)-4-(4-pyridylmethyl)phthalazine;
1-(3-Chloro-4-fluoroanilino)-4-(4-pyridylmethyl)phthalazine; and
1-(3-Methylanilino)-4-(4-pyridylmethyl)phthalazine.

A compound useful in the practice of the invention may be prepared by processes known per se for example as described in the working examples infra.

The present invention relates also to pharmaceutical compositions that comprise a compound of formula I (or an N-oxide thereof) as active ingredient and that can be used in the treatment of ERM formation and retinal detachment. Compositions for topical ocular or enteral administration, such as nasal, buccal, rectal, or, especially, oral administration, and for parenteral administration, such as intravenous, intramuscular, intravitreal, sub-conjunctival or subcutaneous administration, to warm-blooded animals, especially humans, are preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampules, vials, suppositories, or capsules. Further dosage forms are, for example, ointments, creams, pastes, foams, tinctures, lip-sticks, drops, sprays, dispersions, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

For topical ocular application, preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, for example Tween 80 (polyoxyethylene(20)sorbitan mono-oleate; trademark of ICI Americas, Inc, USA).

Preferably, the formulation will comprise polymers such as hydroxypropylmethyl cellulose, acrylic acid homo- and co-polymers such as commercially available Carbopols from BF Goodrich, sodium carboxymethylcellulose, carboxymethylcellulose, dextran, polyvinylpyrrolidone, or gelatins.

Compositions useful in the methods of the present invention may further comprise a tonicity enhancing agent, Such tonicity enhancing agents may include compounds such as urea, glycerol, sorbitol, mannitol, propylene glycol, or dextrose. Such tonicity enhancing agent is added to impart an osmolality of approximately 50 to 500 mOsmol, more preferred from 200 to 350 mOsmol.

A non-ionic surfactant such as polysorbate 80 (polyoxyethylene(20)sorbitan monooleate) may be incorporated to reduce the cohesion force between drug particles.

Addition of an acceptable buffer system is generally advantageous. Examples of buffer substances include tromethamine (tris-(hydroxymethyl)-aminomethane, TRIS). The pH range is generally in the range of from 4 to 8 and more preferably from 7.0 to 7.8.

The composition may further comprise a preservative, e.g. to inhibit microbial growth upon storage. A non-limiting selection of preservatives includes a quaternary ammonium compound such as benzalkonium chloride, cetrimide or the like, stabilized oxychloro complexes such as the commercially available Purite, stabilized perborate, Polyquat or mixtures thereof.

An exemplary topical ocular pharmaceutical composition useful in the practice of the invention is set forth in Table 1:

TABLE 1

| Ingredient | % w/v | mg/mL |
|---|---|---|
| PTK 787 | 1.0 | 10 mg/mL |
| Polysorbate 80 | 0.1 | 1.0 mg/mL |
| Carbopol 980 NF | 0.25 | 2.5 mg/mL |
| Hydroxypropylmethyl cellulose | 0.3 | 3.0 mg/mL |
| Sorbitol | 3.43 | 34.3 mg/mL |
| Benzalkonium Chloride NF | 0.015 | 0.15 mg/mL |

TABLE 1-continued

| Ingredient | % w/v | mg/mL |
| --- | --- | --- |
| Sodium Hydroxide | Adjust to pH 6.8–7.2 | Adjust to pH 6.8–7.2 |
| Water for Injection | Qs to 100 | Qs to volume |

Topical ocular compositions used in the practice of the methods of the invention can be administered, e.g., one, two, three, or four times daily, where each administration comprises one, two, three, four, or five drops per eye.

Suitable carriers for oral dosage forms are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

In the case of an individual having a bodyweight of about 70 kg the daily oral dose administered is from approximately 0.1 g to approximately 5 g, preferably from approximately 0.5 g to approximately 2 g, of a compound of the present invention.

Some methods for synthesizing compounds useful in the practice of the present invention are as follows. Temperatures are measured in degrees celsius. Unless otherwise indicated, the reactions take place at room temperature.

The short forms and abbreviations used have the following definitions:

| | |
| --- | --- |
| DMSO | dimethyl sulfoxide |
| ESI-MS | electrospray ionization mass spectroscopy |
| Ether | diethyl ether |
| h | hour(s) |
| HV | high vacuum |
| RE | rotary evaporator |
| RT | room temperature |
| m.p. | melting point |
| THF | tetrahydrofuran |

1-(4-Chloroanilino)-4-(4-pyridylmethyl)phthalazine dihydrochloride

A mixture of 15.22 g (59.52 mmol) 1-chloro-4-(4-pyridylmethyl)phthalazine (for preparation see German Auslegeschrift no. 1 061 788 [published 23 Jul. 1959]), 7.73 g (60.59 mmol) 4-chloroaniline and 200 ml 1-butanol is heated for 2 h under reflux. The crystallizate which is obtained when the mixture slowly cools to 5° C. is then filtered off and washed with 1-butanol and ether. The filter residue is dissolved in about 200 ml hot methanol, the solution is treated with 0.75 g activated carbon and filtered via a Hyflo Super Cel, and the pH of the filtrate is adjusted to about 2.5 with 7 ml 3N methanolic HCl. The filtrate is evaporated to about half the original volume and ether added until slight turbidity occurs; cooling then leads to the precipitation of crystals. The crystallizate is filtered off, washed with a mixture of methanol/ether (1:2) as well as ether, dried for 8 h at 110° C. under HV, and equilibrated for 72 h at 20° C. and in room atmosphere. In this way, the title compound is obtained with a water content of 8.6%; m.p. >270° C.; 1H NMR (DMSO-d6) 11.05-12.20 (br), 9.18-9.23 (m, 1H), 8.88 (d, 2H), 8.35-8.40 (m, 1H), 8.18-8.29 (m, 2H), 8.02 (d, 2H), 7.73 (d, 2H), 7.61 (d, 2H), 5.02 (s, 2H); ESI-MS: (M+H)+=347.

1-(4-Chloroanilino)-4-(4-pyridylmethyl)phthalazine hydrochloride

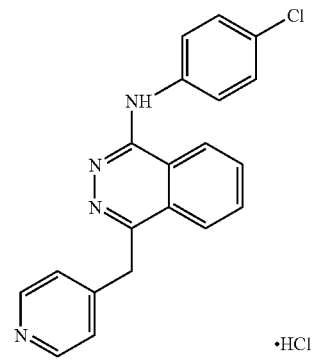

A mixture of 0.972 g (3.8 mmol) 1-chloro-4-(4-pyridylmethyl)phthalazine, 0.656 g (4 mmol) 4-chloroaniline hydrochloride (Research Organics, Inc., Cleveland, Ohio, USA) and 20 ml ethanol is heated for 2 h under reflux. The reaction mixture is cooled in an ice bath, filtered, and the crystallizate washed with a little ethanol and ether. After drying under HV for 8 h at 110° C. and for 10 h at 150° C., the title compound is obtained as a result of thermal removal of HCl; m.p. >270° C.; 1H NMR (DMSO-d6) 9.80-11.40 (br), 8.89-8.94 (m, 1H), 8.67 (d, 2H), 8.25-8.30 (m, 1H), 8.06-8.17 (m, 2H), 7.8 (d, 2H), 7.69 (d, 2H), 7.49 (d, 2H), 4.81 (s, 2H); ESI-MS: (M+H)+=347.

1-(4-Chloroanilino)-4-(4-pyridylmethyl)phthalazine hydrochloride

A mixture of 1.28 g (5 mmol) 1-chloro-4-(4-pyridylmethyl)phthalazine, 0.67 g (5.25 mmol) 4-chloroaniline and 15 ml 1-butanol is heated for 0.5 h at 100 h while stirring in a nitrogen atmosphere. The mixture is then cooled to RT, filtered, and the filtrate washed with 1-butanol and ether. For purification, the crystallizate is dissolved in 40 ml of hot methanol, the solution treated with activated carbon, filtered via Hyflo Super Cel, and the filtrate evaporated to about half its original volume, resulting in the formation of a crystalline precipitate. After cooling to 0° C., filtration, washing of the filter residue with ether, and drying under HV for 8 h at 130° C., the title compound is obtained; m.p.>270° C.; 1H NMR (DMSO-d6) 9.80-11.40 (br), 8.89-8.94 (m, 1H), 8.67 (d, 2H), 8.25-8.30 (m, 1H), 8.06-8.17 (m, 2H), 7.87 (d, 2H), 7.69 (d, 2H), 7.49 (d, 2H), 4.81 (s, 2H); ESI-MS: (M+H)+= 347.

1-(4-Chloroanilino)-4-(4-pyridylmethyl)phthalazine

A mixture of 14.19 g (0.1 mol) phosphorus pentoxide, 13.77 g (0.1 mol) triethylamine hydrochloride and 12.76 g (0.1 mol) 4-chloroaniline is heated and stirred in a nitrogen atmosphere at 200° C. until a homogeneous melt has formed (about 20 min). To the melt, 5.93 g (0.025 mol) 4-(4-pyridylmethyl)-1(2H)-phthalazinone (for preparation see German Auslegeschrift no. 1 061 788 [published 23 Jul. 1959]) is added, and the reaction mixture is stirred for 3 h at 200° C. After the reaction mixture has cooled to about 100° C., 200 ml of water is added. Stirring is continued until the temperature reaches about 30° C., and then 20 ml conc. ammonia (30% aqueous ammonium hydroxide solution) and 900 ml chloroform are added consecutively. As soon as a diphasic mixture has formed, the organic phase is separated off, dried over anhydrous sodium sulfate, filtered, and the filtrate evaporated on a RE to a volume of about 50 ml, to which 100 ml acetate is then added, and the mixture is cooled in an ice bath. The crystallizate obtained is filtered off and washed with acetate and ether. After recrystallization from methanol and drying under HV for 8 h at 120° C., the title compound is obtained; m.p. 194-195° C.; ESI-MS: (M+H)+=347.

Most preferred is a compound with the following structure, also referred to herein as PTK787:

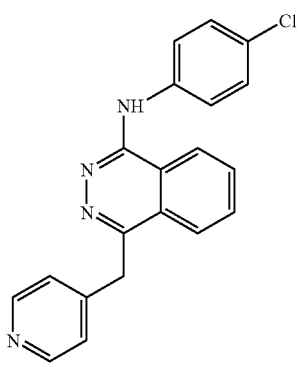

CGP 79787D

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

EXAMPLES

Mice are treated humanely in accordance with Association for Research in Vision and Ophthalmology guidelines for the use of animals in ophthalmic and vision research. Reference to P(x) refers to postnatal day (x). Methods for the generation and characterization of rho/PDGF-A and rho/PDGF-B transgenic mice are known to those of ordinary skill. Hemizygous rho/PDGF-B, line 1 mice in a C57BL/6 background and homozygous rho/PDGF-A, line 2 mice in a C57BL/6 background are each divided into 5 groups and starting on P7 are treated by gavage once a day with vehicle or vehicle containing 50 mg/kg of PKC412, PTK787, SU1498, or Imatinib mesylate. Rho/PDGF-B mice are euthanized at P12 to assess ERM formation by staining with Griffonia simplicifolia lectin (GSA), which selectively stains vascular cells, or at P21 to assess for retinal detachment. Homozygous rho/PDGF-A mice are euthanized at P40 to assess ERM formation by immunohistochemical staining for glial fibrillary acidic protein (GFAP) or at P50 to assess for retinal detachment.

PKC412 is an inhibitor of the kinase activity of several isoforms of PKC, VEGF receptors, PDGF receptors, and ckit, but not receptors of several other growth factors that have been tested. PTK787 is an inhibitor of the kinase activity of VEGF receptors, PDGF receptors, and ckit, but not receptors of several other growth factors that have been tested. SU1498 is an inhibitor or the kinase activity of VEGF receptors. Imatinib mesylate is an inhibitor of the kinase activity of PDGF receptor kinase, ckit, and vAbl, but not the receptors of several other growth factors.

Rho/PDGF-B mice are euthanized and eyes are rapidly removed and frozen in optimal cutting temperature embedding media (OCT; Miles Diagnostics, Elkhart, Ind.). Ten µm frozen sections are fixed with 4% paraformaldehyde for 30 minutes, washed with 0.05M Tris-buffered saline, pH 7.6 (TBS). Slides are incubated in methanol/$H_2O_2$ for 10 minutes at 4° C., washed with 0.05M TBS, and incubated for 30 minutes in 10% normal porcine serum. Slides are incubated 2 hours at room temperature with biotinylated GSA (Vector Laboratories, Burlingame, Calif.) and after rinsing with 0.05M TBS, they are incubated with avidin coupled to peroxidase (Vector Laboratories) for 45 minutes at room temperature. After a 10 minute wash in 0.05M TBS, slides are incubated with diaminobenzidine (Research Genetics) to give a brown reaction product and counterstained with hematoxylin and eosin.

Immunohistochemical staining of retinas for GFAP labels astrocytes and activated Muller cells. Homozygous rho/PDGF-A mice are euthanized and eye are frozen in OCT. Ten µm frozen sections are fixed with 4% paraformaldehyde for 30 minutes, washed with 0.05M TBS, incubated in methanol/$H_2O_2$ for 10 minutes at 4° C., and washed with 0.05M TBS. Specimens are blocked with 10% normal goat serum (NGS) in 0.05M TBS for 30 minutes at room temperature and then incubated with 1:500 rabbit anti-bovine GFAP in 1% NGS/0.05M TBS and incubated in biotinylated goat anti-rabbit antibody for 30 minutes. After washing, the slides are incubated in streptavidin-phosphatase and developed with HistoMark Red (Kirkegaard and Perry, Gaithersburg, Md.) according to the manufacturer's instructions. Sections are dehydrated and mounted with Cytoseal.

To perform quantitative assessments, 10 µm serial sections are cut through an entire eye starting with sections that included the iris root on one side of the eye and proceeding to the iris root on the other side. Every tenth section, roughly 100 µm apart, is stained with GSA (rho/PDGF-B mice) or anti-GFAP (homozygous rho/PDGF-A mice). Section are examined with an Axioskop microscope with the examiner masked with respect to treatment group. For assessment of the amount of ERM, images are digitized using a 3 CCD color video camera and a frame grabber. Image-Pro Plus software is used to delineate GSA- or GFAP-stained cells in the retina and their area is measured. The mean of the measurements from each eye is used as a single experimental value. For assessment for retinal detachment, sections are examined and graded as to the presence of partial or total retinal detachment. If all stained sections showed total retinal detachment, then the eye is graded as total retinal detachment. If any of the sections show at least a partial retinal detachment, but all sections did not show total retinal detachment, then the eye is graded as partial retinal detachment. If none of the sections show any retinal detachment, then the eye is graded as no retinal detachment.

For analysis of area measurements, data are analyzed using either a generalized linear model with generalized estimating equations (GEE) or analysis of variance (ANOVA) model. The generalized linear model with GEE is analogous to the ANOVA model; the primary difference is that the allows for correlated data from right and left eyes to be included from direct modeling of the correlation, while the ANOVA model requires the data to be independent, hence right and left eye values must be averaged prior to analysis. Findings are similar with each type of analysis and therefore the generalized linear model with GEE is reported. To adjust for multiple comparisons, a p value of 0.0125 is required for statistical significance.

For comparisons between vehicle-treated eyes and eyes in the other treatment groups with regard to retinal detachments, data are analyzed using logistic regression with GEE to account for correlation between eyes. To adjust for multiple comparisons, a p value of 0.0125 is required for statistical significance.

Example 1

PKC412 and PTK787 Reduce ERM Formation in Rho/PDGF-B Mice

Starting at P7, hemizygous rho/PDGF-B mice are given vehicle or vehicle containing 50 mg/kg of PKC412, PTK787, SU1498, or Imatinib mesylate once a day by gavage. Untreated rho/PDGF-B mice consistently develop prominent ERMs by P12 that are best illustrated by staining retinal sections with GSA, and consistent with those previous results extensive GSA-stained ERMs are seen in the eyes of mice treated with vehicle. In contrast, eyes from mice treated with PKC412 or PTK787 have little ERM formation. Eyes from mice treated with SU1498 or Imatinib mesylate have extensive ERM formation, similar to that seen in vehicle-treated eyes. Measurement of the area of GSA staining by image analysis showed significantly smaller areas in PKC412-and PTK787-treated mice compared to vehicle-treated mice, whereas mice treated with SU1498 or Imatinib mesylate showed no significant difference.

Example 2

PTK787 and PKC412 Reduce Retinal Detachments in Rho/PDGF-B Mice

At P21, vehicle-treated mice have extensive ERM formation with multiple layers of ectopic cells in the inner retina and more than 80% of eyes have folding of the outer retina and retinal detachment, with total funnel-shaped detachments in about ⅓ of eyes. Mice treated with 50 mg/kg of PKC412 or PTK787 by gavage between P7 and P21 have mild epiretinal membrane formation and roughly 50% of the eyes have a normal appearing outer retina. Only 10% of eyes from mice treated with PKC412, and 15% from mice treated with PTK787 have total retinal detachments, compared to 35% of eyes in mice treated with vehicle. Mice treated with SU 1498 or Imatinib mesylate have extensive epiretinal membrane formation and nearly 90% have at least partial retinal detachment. Sixty percent of eyes from mice treated with SU1498 and 30% from mice treated with Imatinib mesylate have total retinal detachment.

Due to the many experimental groups requiring multiple comparisons, the decrease in total retinal detachments in the PKC412 and PTK787 groups is not considered statistically significant. An independent experiment is performed to compare treatment with PKC412 to treatment with vehicle. Roughly 10% of eyes of mice treated with PKC412 compared to 55% of eyes of mice treated with vehicle have total retinal detachment at P21, a difference that is highly statistically significant.

Example 3

PKC412 and PTK787 Decrease Epiretinal Membrane Formation and Retinal Detachment in Homozygous rho/PDGF-A Mice Homozygous rho/PDGF-A mice (rho/PDGF-AA mice) develop glial epiretinal membranes that are slowly progressive and often result in traction retinal detachment between 1 and 2 months of age. At P40, eyes from mice treated with vehicle have a thick layer of GFAP-stained cells on the surface of the retina and within the inner nuclear layer. Eyes from mice treated with PKC412 have a layer of glial cells on the surface of the retina, but none or few in the inner nuclear layer and the total area of GFAP staining per section is significantly less than that in vehicle treated eyes. Eyes from mice treated with PTK787 have a layer of GFAP-positive cells on the surface of the retina and occasional clumps in the inner nuclear layer, but the total area of GFAP staining per section is significantly less than that in vehicle-treated eyes. Retinas from mice treated with SU1498 or Imatinib mesylate showed no significant difference from the retinas of vehicle treated mice in GFAP staining.

At P50, the majority of eyes from vehicle-treated mice (more than 60%) showed total, funnel-shaped detachments, whereas the majority of eyes from PKC412-or PTK787-treated mice showed no detachment. Only 10-15% of eyes in the PKC412 or PTK787 groups have total retinal detachments, which is significantly less than that seen in the vehicle group. There is no decrease in total retinal detachments in mice treated with SU 1498 compared to those treated with vehicle, and although there are fewer severe detachments in mice treated with Imatinib mesylate, the difference did not meet the rigorous criterion required for statistical significance given the need for multiple comparisons among the 5 groups.

What is claimed is:

1. A method for the treatment of a subject suffering from ERM (epiretinal membrane) formation or retinal detachment due to ERM formation comprising administering to a subject suffering from ERM formation or retinal detachment due to ERM formation an effective amount of a compound of formula I to treat ERM formation or retinal detachment in the eye of the subject, wherein formula I is $$\text{(I)}$$

(structure shown: phthalazine with X—(CHR)_n—Y at position 1 and Z—CH_2 at position 4)

wherein
n is 0 to 2,
R is H or lower alkyl;
X is imino, oxa, or thia;
Y is aryl; and
Z is unsubstituted or substituted pyridyl,
an N-oxide thereof, wherein 1 or more N atoms carry an oxygen atom,
or a salt thereof.

2. The method of claim 1 wherein said subject is a human.

3. The method of claim 1, wherein
n is 0 or 1,
R is H or lower alkyl,
X is imino, oxa, or thia,
Y is phenyl, lower alkenyl, lower alkoxycarbonyl, lower alkylcarbamoyl, lower alkanoyl, phenyloxy, halogen-lower alkyloxy, lower alkoxycarbonyl, lower alkylmercapto, halogen-lower alkylmercapto, hydroxy-lower alkyl, lower alkylsulfonyl, phenylsulfonyl, halogen-lower alkylsulfonyl, dihydroxybora (—B(OH)$_2$), 2-methylpyrimidin-4-yl, oxazol-5-yl, 2-methyl-1,3-dioxolan-2-yl, 1h-pyrazol-3-yl, 1-methyl-pyrazol-3-yl, lower alkylenedioxy bound to two adjacent C-atoms, pyridyl, or 4-chloro-2-fluoroanilino, wherein said phenyl is unsubstituted or is substituted by one or two substituents independently of one another from the group comprising amino, lower alkanoylamino, halogen, lower alkyl, halogen-lower alkyl, hydroxy, lower alkoxy, phenyl-lower alkoxy, and cyano, and
Z is 3- or 4-pyridyl, lower alkyl, halogen-lower alkyl, lower alkoxy or hydroxy, wherein said pyridyl is unsubstituted or is substituted by one or two substituents independently of one another from the group comprising halogen.

4. The method of claim 1, wherein
n is 0 or 1,
R is H,
X is imino,
Y is phenyl, lower alkanoylamino, helogen, lower alkyl, halogen-lower alkyl, hydroxy, lower alkoxy, phenyl-lower alkoxy, or cyano, wherein said phenyl is unsubstituted or is substituted by one or two substituents independently of one another from the group comprising amino, and
Z is 4-pyridyl, lower alkyl, halogen-lower alkyl, hydroxy and lower alkoxy, wherein pyridyl is unsubstituted or is substituted by a substituent from the group consisting of halogen.

5. The method of claim 1, wherein
n is 0 or 1,
R is H,
X is imino,
Y is phenyl, lower alkyl, halogen-lower alkyl, hydroxy; lower alkoxy, or cyano, wherein phenyl is unsubstituted or is substituted by one or two substituents independently of one another from halogen, and
Z is 4-pyridyl, lower alkyl, halogen-lower alkyl, hydroxy, or lower alkoxy, wherein said pyridyl is substituted or unsubstituted by a halogen.

6. The method of claim 1, wherein
n is 0,
X is imino,
Y is phenyl, methyl, trifluoromethyl, hydroxy, cyano, or methoxy, wherein said phenyl is substituted or unsubstituted by fluorine or chlorine, and
Z is 4-pyridyl, methyl, trifluoromethyl, hydroxy or methoxy, wherein said pyridyl is substituted or unsubstituted by fluorine or chlorine.

7. The method of claim 1, wherein
n is 0,
X is imino,
Y is phenyl, methyl, methoxy, cyano or trifluoromethyl, wherein said phenyl is substituted or unsubstituted by chlorine or fluorine, and
Z is 4-pyridyl or methyl, wherein said pyridyl is substituted or unsubstituted by chlorine or fluorine.

8. The method of claim 1, wherein said compound is selected from the group consisting of:
1-(4-Methylanilino)-4-(4-pyridylmethyl)phthalazine;
1-(4-Chloroanilino)-4-(4-pyridylmethyl)phthalazine;
1-Anilino-4-(4-pyridylmethyl)phthalazine;
1-Benzylamino-4-(4-pyridylmethyl)phthalazine;
1-(4-Methoxyanilino)-4-(4-pyridylmethyl)phthalazine;
1-(3-Benzyloxyanilino)-4-(4-pyridylmethyl)phthalazine;
1-(3-Methoxyanilino)-4-(4-pyridylmethyl)phthalazine;
1-(2-Methoxyanilino)-4-(4-pyridylmethyl)phthalazine;
1-(4-Trifluoromethylanilino)-4-(4-pyridylmethyl)phthalazine;
1-(4-Fluoroanilino)-4-(4-pyridylmethyl)phthalazine;
1-(3-Hydroxyanilino)-4-(4-pyridylmethyl)phthalazine;
1-(4-Hydroxyanilino)-4-(4-pyridylmethyl)phthalazine;
1-(3-Aminoanilino)-4-(4-pyridylmethyl)phthalazine;
1-(3,4-Dichloroanilino)-4-(4-pyridylmethyl)phthalazine;
1-(4-Bromoanilino)-4-(4-pyridylmethyl)phthalazine;
1-(3-Chloro-4-methoxyanilino)-4-(4-pyridylmethyl)phthalazine;
1-(4-Cyanoanilino)-4-(4-pyridylmethyl)phthalazine;
1-(3-Chloro-4-fluoroanilino)-4-(4-pyridylmethyl)phthalazine;
1-(3-Methylanilino)-4-(4-pyridylmethyl)phthalazine; and
pharmaceutically acceptable salts thereof.

9. The method of claim 1, wherein said compound is
1-(4-Chloroanilino)-4-(4-pyridylmethyl)phthalazine and said subject is a human.

10. The method of claim 1, further comprising the administration of a second compound that inhibits VEGF activity wherein said second compound does not have a structure as set out in formula I.

11. The method of claim 10, wherein said second compound is N-benzoyl staurosporine.

12. The method of claim 1, wherein said compound is administered topically to the eye.

13. The method of claim 11, wherein said compound and said second compound are administered topically to the eye.

* * * * *